(12) United States Patent
Adrian et al.

(10) Patent No.: US 8,003,824 B2
(45) Date of Patent: Aug. 23, 2011

(54) PREPARATION OF HYDROQUINONE AMIDE COMPOUNDS WITH ANTIOXIDANT PROPERTIES

(75) Inventors: Guy Adrian, Saint-Genis-Laval (FR); Patrick Bigot, Lyons (FR)

(73) Assignee: Catalys SAS, Lyons Cedex (FR)

( * ) Notice: Subject to any disclaimer, the term of this patent is extended or adjusted under 35 U.S.C. 154(b) by 0 days.

(21) Appl. No.: 12/920,752

(22) PCT Filed: Mar. 6, 2009

(86) PCT No.: PCT/FR2009/000233
§ 371 (c)(1),
(2), (4) Date: Sep. 2, 2010

(87) PCT Pub. No.: WO2009/115707
PCT Pub. Date: Sep. 24, 2009

(65) Prior Publication Data
US 2011/0021820 A1    Jan. 27, 2011

(30) Foreign Application Priority Data
Mar. 7, 2008   (FR) .................................... 08 01246

(51) Int. Cl.
*C07C 233/05* (2006.01)

(52) U.S. Cl. ........................................... 564/170
(58) Field of Classification Search .................. 564/170
See application file for complete search history.

(56) References Cited

U.S. PATENT DOCUMENTS
2007/0281991 A1 * 12/2007 Adrian et al. ................. 514/456
* cited by examiner

*Primary Examiner* — Shailendra Kumar
(74) *Attorney, Agent, or Firm* — Lowenstein Sandler PC

(57) ABSTRACT

The present invention relates to the preparation of compounds of formula (I) derived from arylacetic acid comprising two phenol functions and an amide function, which have free-radical scavenging and antioxidant properties and which are soluble in lipid media. These compounds can be used as cosmetic and pharmaceutical preparations for the prevention of biological degradations caused by free radicals.

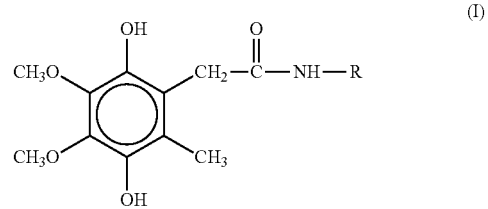

11 Claims, No Drawings

PREPARATION OF HYDROQUINONE AMIDE COMPOUNDS WITH ANTIOXIDANT PROPERTIES

This application is a 371 of PCT/FR2009/000233, filed Mar. 6, 2009.

The present invention concerns the preparation of hydroquinone-amide compounds that have antioxidant properties derived from an arylacetic acid comprising at least two hydroxy and amine or amino-alcohol groups that correspond to formula (I)

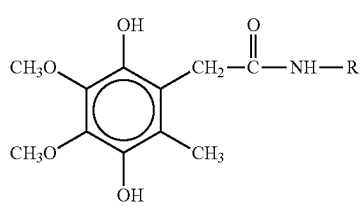

with R=alkyl ($-C_nH_{2n+1}$)
or R=hydroxyalkyl ($-C_nH_{n2+1}O$)
or R=dihydroxyalkyl ($-C_nH_{n2+1}O_2$)
n being a number between 1 and 30.

Compounds (I) have the aromatic structure of reduced or ubiquinol coenzymes Q of formula (II)

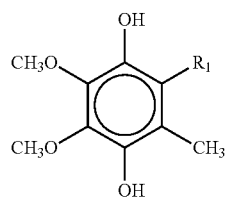

which are themselves a reduced form of coenzymes Q or ubiquinones of formula (III), known for their antioxidant and free radical inhibiting properties in humans ([in English:] B. Halliwell and J. Gutteridge—Free Radicals in Biology and Medicine—1998).

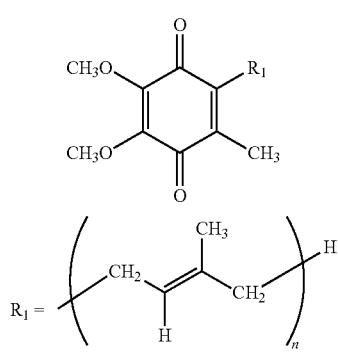

Ubiquinones or coenzymes $Q_n$, where n is the number of isoprene units in the $R_1$ chain, are lipophilic molecules made up of benzoquinone and a hydrophobic trans-polyisoprene chain that ensures stability in an organic medium.

In humans especially, the coenzyme $Q_{10}$ of formula (III) with n=10, after in vivo reduction in hydroquinone of formula (II) per the reversible reaction (1), is involved in mitochondria during cellular respiration, in the production of adenosine triphosphate (ATP), and in slowing cellular aging by capturing free radicals per reaction (2).

([In English:] S. Yamashita—Detection of ubiquinol and ubiquinone as a marker of oxidative stress, Anal. Biochemistry, 1997, 250 p. 66).

Reaction (1)

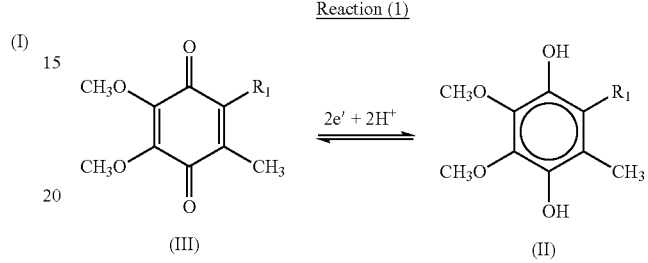

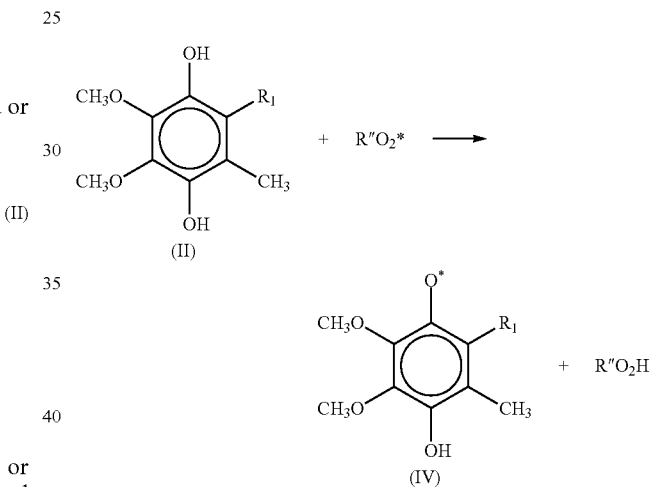

The compounds (III) are obtained industrially through costly fermentation or multiple-step synthesis, which limits their use on a large scale as an antioxidant for the prevention of degenerative diseases and human aging—the appearance of skin (wrinkles), cardiovascular diseases, neurodegenerative diseases and cancers—by efficiently capturing the free radicals that degrade cellular membranes and lipoproteins.

The object of the invention is to obtain antioxidant compounds that have the above properties, are stable and non-toxic, miscible in both lipid and aqueous media, which can effectively penetrate into cutaneous tissues.

These compounds (I) have the aromatic nucleus of ubiquinols (II) and lend themselves to the oxidation-reduction reaction (1).

They are obtained through the amidation of dihydroxy-2,5 dimethoxy-3,4 methyl-5 benzene acetic acid (V) in the form of its cyclic derivative (VI), by condensation with an amine of formula $RNH_2$ where R represents:

either a linear or branched R' alkyl chain comprising 1 to 30 carbon atoms: formula (Ia), or a hydroxy alkyl chain:

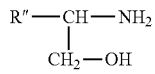
(VII)

in which R″ is a hydrogen atom or a linear or branched chain of 1 to 28 carbon atoms.

For the uses cited above, amino-2-dodecanol-1 is preferred, with

R″=decyl (n-$C_{10}H_{21}$): formula (Ib).

or a dihydroxy alkyl chain:

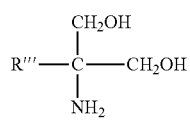
(VIII)

in which R‴ is a hydrogen atom or a linear or branched chain of 1 to 27 carbon atoms.

For the uses cited above, amino-2 propane diol-1,3 is preferred, with R‴=H: formula (Ic).

Amides (I) from amines R′$NH_2$ or amino-alcohols (VII) or (VIII) are formed through the simple heating in the absence of air of a molar equivalent of phenol lactone (VI) in a solvent medium:

reaction (3).

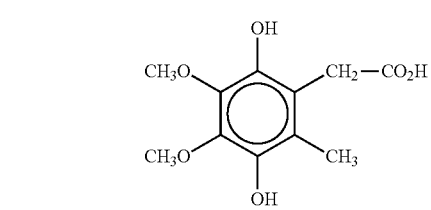
(V)

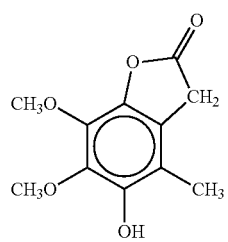
(VI)

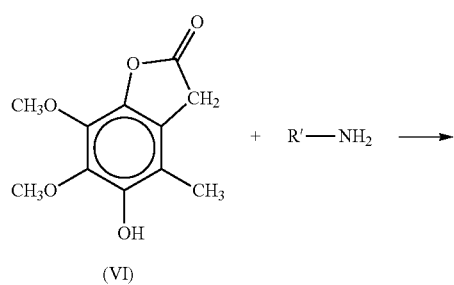
(VI)

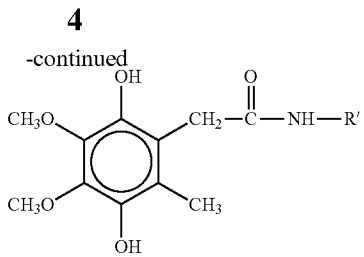
(Ia)

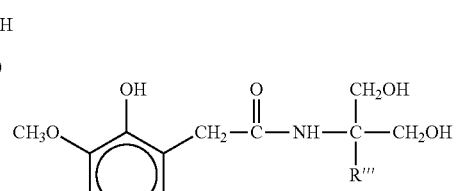
(VI)

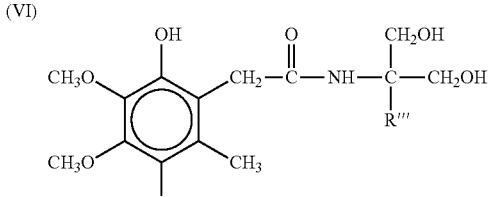
(Ib)

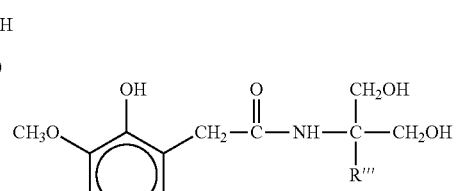
(VI)

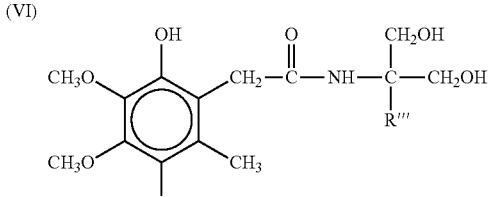
(Ic)

Lactone phenol (VI) has only been described once (V. G. Ramsey, Journal of the American Chemical Society, 1966, p. 1553).

It is obtained through the ozonolysis of coenzyme $Q_9$ (formula (III) with n=9), reduction with zinc, acetylation and then hydrolysis in an acid medium.

The high cost of the raw material along with the danger associated with the industrial use of ozone led us to develop a new method of synthesizing the compound (VI), in 3 stages, from coenzyme $Q_0$ (formula (III) with n=0), an industrial raw material of coenzyme $Q_{10}$, through reduction in hydroquinone of formula (II) in which $R_1$=H.

This reduction is conducted in sodium dithionite in an aqueous medium with quantitative yield.

Condensation with ethyl glyoxylate in the presence of a Lewis acid, especially titanium tetrachloride between −10° C.

and 60° C. and particularly at 0° C., enables the new compound (IX) to be obtained with a quantitative yield (Synthesis 2004, p. 760).

The hydrogenation of (IX) in the presence of palladium on carbon in an acid medium like acetic acid in the presence of a strong acid and in particular in the presence of sulfuric acid between 0° C. and 120° C., preferably at 90° C., leads directly to lactone (VI) with an isolated yield of 68% from coenzyme $Q_0$: reaction (4):

Reaction (4)

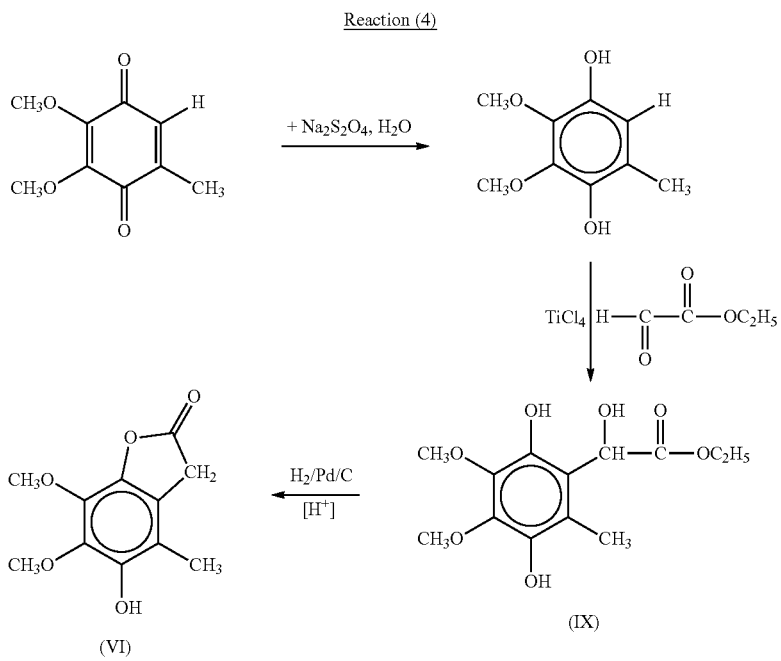

Lactone (VI), a solid, stable compound, is unexpectedly and advantageously directly condensed with the $RNH_2$ amines, without activation or protection of the free phenol function, leading directly to compounds (I).

The reaction of the amines or amino-alcohols with (VI) is performed through simple heating between 50° C. and 150° C. in an aprotic polar solvent like N-methylpyrrolidone, dimethylformamide or pyridine, in the absence of oxygen and preferably in the presence of a reducing agent such as an alkaline sulfite and preferably sodium dithionite.

After hydrolysis, the hydroquinone-amides (I) are isolated using appropriate techniques and purified through crystallization.

The compounds (I), stable as a solid, oxidize in the presence of oxygen in solution or in the presence of oxidizing agents, leading to quinone-amides (X).

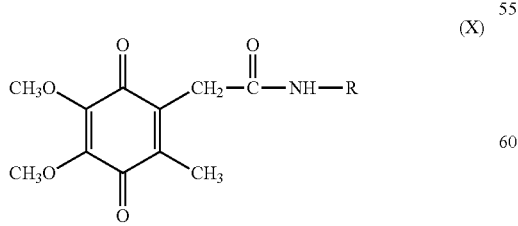

(X)

The preferred oxidizing agent is iron chloride in an alcohol-water medium between 0° C. and 80° C., preferably in an ethanol-water medium at 20° C.

The antioxidant potential in solution of the compounds (I) is evaluated by measuring their reaction with the free radical diphenyl-picryl-hydrazide (XI) per C. T. Ho, S. Agric. Food Chem. 1999, p. 3975, using methyl gallate as a reference (XII).

The compounds (I) as a whole show antioxidant activity similar to that of the reference.

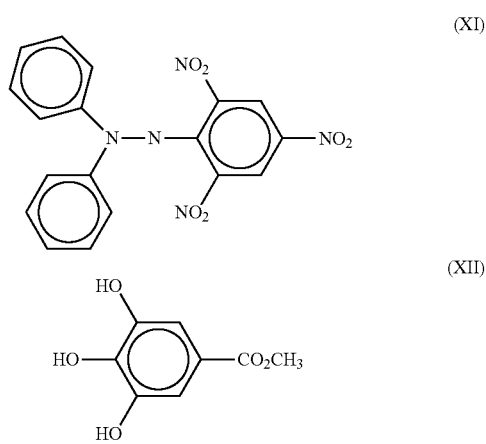

Applicant developed a process for preparing hydroquinone-amide compounds with antioxidant properties.

These compounds can be made into tablets, capsules, or as a mixture in cosmetic or pharmaceutical preparations using the usual techniques.

Of course, one skilled in the art can make various modifications to the devices or processes just described only as non-limiting examples, without leaving the framework of the invention.

The invention is illustrated by the following examples 1 to 5:

EXAMPLE 1

Obtaining Lactone of Formula (VI) from dimethoxy-2,3 methyl-5 benzoquinone-1,4 (Coenzyme $Q_0$)

We prepared a solution of 9.2 g (0.0505 mole) of dimethoxy-2,3 methyl-5 benzoquinone-1,4 in 100 mL of ethyl acetate at 20° C.

We added a solution of 31 g (0.178 mole) of sodium dithionite to 150 mL of water and stirred for 30 minutes.

The red medium turns pale yellow.

The organic phase was separated and concentrated in a vacuum to obtain 9.2 g of beige solid.

MP=77° C.

This solid was dissolved in 70 mL of dichloromethane, cooled to 0° C.

Next, a commercial solution of 10.7 g (0.0525 mole) of 50% ethyl glyoxylate in toluene was added, followed by 5.5 mL (0.05 mole) of titanium chloride.

The purple mixture was stirred for 15 minutes at 0° C., then hydrolyzed with 100 mL of water.

The lower organic phase was concentrated to obtain 16.5 g of a brown oil, which was used without purification.

This raw compound (IX) was dissolved in 140 mL of acetic acid and placed in a 250 mL autoclave with 1.5 g of 10% palladium catalyzer on carbon and 80 mg of concentrated sulfuric acid.

The mixture was heated to 90° C. under 6 bars of hydrogen pressure and stirred for 3 hours.

After cooling, the mixture was filtered and then concentrated under reduced pressure.

The residue was crystallized in 30 mL of diisopropylether to obtain 8.3 g of gray solid.

MP=140° C.

Yield=68% from $Q_0$.

EXAMPLE 2

Obtaining Amide (Ia) in which $R'=nC_8H_{17}$

We prepared a solution of lactone (VI) obtained using Example 1:

2 g (8.03 mmole) in 20 mL of pyridine, we added 1.0 g (7.8 mmole) of n-octylamine and 2.14 g (10.4 mmole) of sodium dithionite.

The green heterogenous mixture was heated to 90° C. and stirred for 1 hour under nitrogen atmosphere, then cooled, hydrolyzed with 50 mL of water and extracted with 100 mL of chloroform.

The organic phase was washed with 60 mL of aqueous 5N hydrochloric acid and then concentrated in a vacuum, leading to a residue that was crystallized in 20 mL of diisopropylether to obtain 1.17 g of white solid.

MP=92-93° C.

Yield=36% from the n-octylamine.

In the same manner, the n-decylamine and the n-dodecylamine were condensed with the formula (VI) lactone to obtain the following results:

| Amine | MP (° C.) | Isolated Yield |
|---|---|---|
| $R' = nC_{10}H_{21}$ | 99-100 | 52% |
| $R' = nC_{12}H_{25}$ | 114 | 61% |

EXAMPLE 3

Obtaining Amide (Ib) in which $R''=nC_{10}H_{21}$

Operating procedures as in Example 2, using amino-2 dodecanol-1 as the amine, led to the amide (Ib), with $R''=nC_{10}H_{21}$.

MP=141-142° C.

Yield=55% from amino-2 dodecanol-1.

EXAMPLE 4

Obtaining Amide (Ic) in which $R'''=H$

Operating procedures as in Example 2, using amino-2 propanediol-1,3 as the amine, led to the amide (Ic), $R'''=H$, isolated after silica gel chromatography using a 95/5 dichloromethane-methanol mixture in oil form.

NMR $^1H$ titer=93%

Yield=17% from amino-2 propanediol-1,3.

The inhibiting effect of free radicals claimed for compounds (Ia) and (Ib) obtained in a pure state was evaluated by measuring their absorbance in UV spectrophotometry at 516 nanometers in the presence of radical diphenyl picryl hydrazide (XI).

We prepared ethanolic solutions containing 200 micromoles per liter of the compound to be tested and 100 micromoles per liter of radical (XI), stirred for 30 minutes at 20° C. and placed in a 1-cm long vessel, and we measured the absorbances.

a) Demonstration of inhibiting effect compared to reference:

| | Methyl gallate | Amide (Ib) | (Ia) $R' = C_{12}H_{25}$ | (Ia) $R' = C_{10}H_{21}$ | (Ia) $R' = C_8H_{17}$ |
|---|---|---|---|---|---|
| Absorbance at 516 nm | 0.06 | 0.06 | 0.06 | 0.06 | 0.06 | b) Assay of the free radical scavenging activity of amides (Ia) and (Ib):

Under absorbance measurement conditions of 516 nanometers, we placed 2 micromoles of reference or substrate (Ia) and (Ib) under the UV cell.

We introduced a solution of 200 micromoles of radical (XI) until the purple color characteristic of the radical and measured the absorbance of the medium:

|  | Methyl gallate | Amide (Ib) | (Ia) R' = C$_{12}$H$_{25}$ | (Ia) R' = C$_{10}$H$_{21}$ | (Ia) R' = C$_8$H$_{17}$ |
|---|---|---|---|---|---|
| (XI) consumed | 27.7 mL | 14.1 mL | 14.7 mL | 14.3 mL | 14.5 mL |
| Absorbance at 516 nm | 0.34 | 0.52 | 0.34 | 0.39 | 0.45 |

The new compounds (Ia) and (Ib) showed similar anti-free radical activity which corresponded in molar equivalent to one-half that of the methyl gallate used as a reference.

EXAMPLE 5

Oxidation of hydroquinone-amides (I) in quinones (X) in which R'=nC$_8$H$_{17}$

We prepared a solution of the compound (Ia) in which R=nC$_8$H$_{17}$ per Example 2:
60 mg (0.17 mmole) in 4.5 mL of ethanol and 0.5 mL of water.
We added 27.5 mg (0.17 mmole) of iron chloride.
The mixture was stirred under air flow for 2 hours at 20° C.
The medium was concentrated under a vacuum, redissolved in 20 mL of ethyl acetate and washed with 10 mL of a 1N aqueous solution of hydrochloric acid.
The organic phase was concentrated to obtain 57 mg of yellow solid.
MP=103-104° C.
Yield=95% from the hydroquinone-amide.
The same oxidation technique applied to the hydroquinone-amide (I) compounds in Examples 2, 3 and 4 led to the following results:

|  |  | MP (° C.) | Yield |
|---|---|---|---|
| Amide (Ia) | R' = C$_{10}$H$_{21}$ | 100-101 | 98 |
|  | R' = C$_{12}$H$_{25}$ | 108-109 | 97 |
| Amide (Ib) | R'' = C$_{10}$H$_{21}$ | 134-135 | 95 |
| Amide (Ic) | R''' = H | oil | 98 |

The invention claimed is:

1. Hydroquinone-amide compounds derived from an arylacetic acid comprising at least 2 hydroxy and amine or amino-alcohol groups corresponding to formula (I)

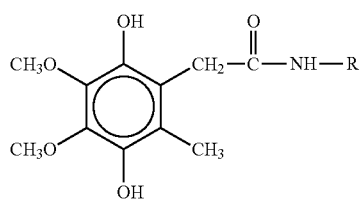
(I)

with R=alkyl(—C$_n$H$_{2n+1}$)
or R=hydroxyalkyl(—C$_n$H$_{2n+1}$O)
or R=dihydroxyalkyl (—C$_n$H$_{2n+1}$O$_2$)
n being a number between 1 and 30.

2. Process for preparing hydroquinone-amide compounds of formula (I) as in claim (1) in which dihydroxy-2,5 dimethoxy-3,4 methyl-6 benzene acetic acid in the form of lactone (VI) is reacted with an amine, an amino-alcohol or an amino-alkanediol

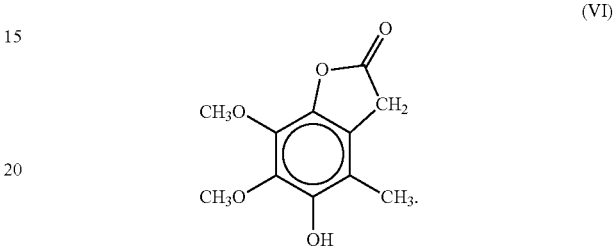
(VI)

3. Process in accordance with claim 2 in which the R group of formula (I) is composed of a linear or branched R' chain containing from 1 to 30 carbon atoms, leading to compounds (Ia)

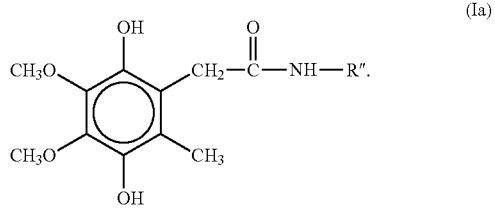
(Ia)

4. Process in accordance with claim 2 in which the R group of formula (I) is composed of a hydroxyalkyl chain in which the R'' substitute is a hydrogen atom or a linear or branched alkyl chain of 1 to 28 carbon atoms, leading to compounds (Ib)

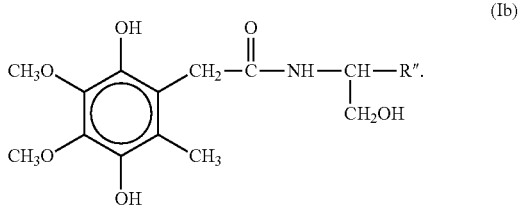
(Ib)

5. Process in accordance with claim 2 in which the R group of formula (I) is composed of a dihydroxyalkyl chain in which the R''' substitute is a hydrogen atom or a linear or branched alkyl chain of 1 to 27 carbon atoms, leading to compounds (Ic).

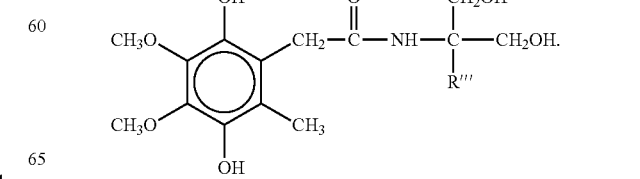
(Ic)

6. Process for obtaining and purifying formula (I) hydroquinone-amide compounds in accordance with claim 2 in which the $RNH_2$ amine compounds are condensed with the lactone derivative (VI) by heating in an aprotic polar solvent in the presence of a reducing agent, followed by hydrolysis and crystallization or chromatography.

7. Process in accordance with claim 2 in which the temperature of the condensation medium is between 50° C. and 150° C.

8. Process in accordance with claim 6 in which the temperature of the condensation medium is between 50° C. and 150° C.

9. Process in accordance with claim 2 in which condensation is performed in the presence of a reducing agent from the alkaline sulfite group.

10. Process in accordance with claim 6 in which condensation is performed in the presence of a reducing agent from the alkaline sulfite group.

11. Process in accordance with claim 7 in which condensation is performed in the presence of a reducing agent from the alkaline sulfite group.

* * * * *